United States Patent [19]

Sasaki et al.

[11] 4,390,468

[45] Jun. 28, 1983

[54] PREPARATION OF ANTITUMOR AGENT FROM SHELLFISH

[75] Inventors: Takuma Sasaki, Tokyo; Kazuya Nakamichi, Sohka, both of Japan

[73] Assignee: Maruzen Oil Co., Ltd., Osaka, Japan

[21] Appl. No.: 404,971

[22] Filed: Aug. 4, 1982

[51] Int. Cl.³ .......................... A23J 1/04; C07G 7/00
[52] U.S. Cl. ................................ 260/112 R; 424/95; 424/177
[58] Field of Search ..................................... 260/112 R

[56] References Cited

U.S. PATENT DOCUMENTS 3,862,122  1/1975  Peniston et al. ............ 260/112 R X
4,199,496  4/1980  Peniston et al. ................ 260/112 R

OTHER PUBLICATIONS

J. of National Cancer Institute, vol. 60, No. 6, pp. 1499–1500, Jun. 1978, Sasaki et al.

Primary Examiner—Howard E. Schain
Attorney, Agent, or Firm—Larson & Taylor

[57] ABSTRACT

A new antitumor agent is provided which consists essentially of water-soluble, macromolecular glycoprotein substances having a range of molecular weights within the limits of from 10,000 to 300,000 and which is prepared from shellfish or mollusc by taking up the liquid portion which comes from the cooking of raw shellfish in an aqueous solvent, typically water or a saline solution, or vapor of such solvent and which is to be discarded as waste, concentrating the liquid portion to a smaller volume or to dryness, dissolving the resulting concentrate or dry powder in an aqueous solvent and isolating the desired water-soluble, macromolecular glycoprotein substances therefrom. The isolation of the desired substances is preferably carried out by an ion-exchange chromatography with a basic anion-exchanger followed by a gel-filtration.

10 Claims, 5 Drawing Figures

PREPARATION OF ANTITUMOR AGENT FROM SHELLFISH

FIELD OF THE INVENTION

This invention relates to a process for the preparation of an antitumor agent from shellfish or mollusc on a large scale and to the antitumor agent thus prepared.

BACKGROUND OF THE INVENTION

Most of known antitumor agents are of low molecular weights and rely on their direct cytotoxic effect on tumor cells in vivo, so that they have a high toxicity against host animals, giving unfavorable effect thereon. On the other hand, some polysaccharides having a relatively high molecular weight, a low toxicity and significant immunopotenciating and antitumor properties have been used in the form of a partially purified powder derived from diverse sources including higher plants, fungi, lichen, bacteria and yeasts by extraction, but they are narrow in antitumor spectra and thus have limited applications in practical purposes.

It has already been reported that some antitumor materials are obtained from shellfish (see Japanese Patent Publication No. 8088/82 and Japanese Patent KOKAI Nos. 41314/79 and 41315/79). According to these publications, the antitumor materials are prepared by a process comprising (1) removing shells from raw shellfish with or without heating the latter, (2) removing the liver from the meat, (3) finely cutting or grinding the resulting meat in an aqueous solvent such as water and a saline solution at a low temperature by means of a blender and the like, optionally followed by sonication or other physical impact treatment whereby to attain high homogenization of the finely divided meat pieces with good extraction of desired antitumor materials in the cold aqueous solvent, (4) removing all the water-insoluble materials including the exhausted meat pieces from the resulting mixture by centrifuging or other means and (5) isolating the desired antitumor materials from the extract thus obtained by purification means known for the isolation of protein substances such as dialysis, ultrafiltration, gel-filtration and column chromatography. The antitumor materials thus obtained from shellfish are interested in that they have broad antitumor spectra and high therapeutic activities. However, the processes hitherto proposed for the preparation of these materials as above-mentioned have such disadvantages that they have to spend the edible portions of shellfish being expensive, require complicated procedures for the extraction of desired materials and involve problems on disposal of the spent residue of meat pieces in large amount, so that it seems difficult to provide these materials on an industrial scale through these processes.

We have made our investigations with the intention of providing a process acceptable for the purpose of industrial production of antitumor materials of a kind similar to those derived from the meat of shellfish as above-mentioned and have now found that the liquid portion which comes from cooking of raw shellfish carried out in a hot aqueous solvent or with vapor of such solvent to take up edible portion thereof and which is to be discarded as waste can serve as raw material from which water-soluble, macromolecular glycoprotein substances useful as antitumor agent is recovered and that these substances have a range of molecular weights within the limits of from 10,000 to 300,000 and can be recovered efficiently by certain combination of purification techniques. The liquid portion coming from cooking of raw shellfish has hiterto been discarded as waste with costly additional treatment required to avoid environmental contamination and is hereinafter referred to as "waste liquor".

SUMMARY OF THE INVENTION

Accordingly, it is the main object of this invention to provide a process for the preparation of an antitumor agent from waste liquor, i.e. the liquid portion coming from cooking of raw shellfish. Another object of this invention is to provide an antitumor agent consisting essentially of water-soluble, macromolecular glycoprotein substances having a range of molecular weights within the limits of from 10,000 to 300,000. These and other objects of this invention will become clear from the following descriptions.

According to the general aspect of this invention, therefore, there is provided a process for the preparation of an antitumor agent containing essentially of water-soluble, macromolecular glycoprotein substances having a range of molecular weights within the limits of from 10,000 to 300,000 from shellfish which comprises recovering the liquid portion which comes from cooling of raw shellfish in a hot aqueous solvent or with vapor of such solvent and which is to be discarded as waste, concentrating the liquid portion thus recovered to a smaller volume or to dryness to yield a concentrate or dry powder and isolating the water-soluble, macromolecular glycoprotein substances from the concentrate or dry powder.

BRIEF DESCRIPTION OF THE DRAWINGS

FIGS. 1 and 2 show two examples of elution pattern depicted on elution with various concentrations of aqueous sodium chloride solution of substances adsorbed on a basic anion-exchanger in ion-exchange chromatography of an aqueous solution of dry powder derived from waste liquor of cooking of raw scallop, wherein the abscissa axis represents fraction numbers of the eluate, the ordinate axis represents absorbance shown as optical density, the white circles show absorbance at wave length of 490 nm of each eluate fraction colored by the method of Dubois et al. (see J.Anal. Chem., 28, 350~356 (1956)) as an indicator of the carbohydrate content of fractions and the black circles show absorbance at wave length of 750 nm of each eluate fraction colored by Lowry method as an indicator of the protein content of fractions.

DETAILED DESCRIPTION OF THE INVENTION

The liquid portion coming from cooking of raw shellfish to be used as starting material according to the process of this invention may include those by-produced when fresh or raw shellfish which may have been heated, if desired, is cooked or heat-treated in a hot aqueous solvent or with vapor of such solvent for the purpose of obtaining edible portions thereof. The hot aqueous solvent to be used as heating medium may include hot or boiling water, steam and other hot aqueous solvents and vapor of such solvents.

The term "shellfish" used herein includes not only those so-called in a narrow sense, i.e. those having outer shell from among Phylum Mollusca, but also those so-called in broad sense, i.e. any of Moullusca including those living in sea and fresh water. Examples of shellfish are an abaline (*Haliotis discus*), a horned turban (*Batillus cornutus*), a mud-snail (*Cipangopaludina chinensis malleata*), *Semisulcospira libertina*, a hepatic moon shell (*Neverita (Glossaulax) didyma*), an ivory shell (*Babylonia japonica*), a ribbed ark shell (*Scapharca broughtonii*), a Japanese scallop (*Pecten albicans*), a scallop (*Patinopecten yessoensis*), a pearl oyster (*Pinctada fucata*), hard shell mussel (*Mytilus coruscus*), an Asian hard clam (*Meretrix lusoria*), a Japanese little neck (*Tapes philippinarum*), a surf clam (*Mactra chinensis*), a silver mouthed turban shell (*Marmarostoma argyrostoma*), *Turbo petholatus reevei*, and *Meretrix lamarcki*.

The step for preparing the starting material to be used according to this invention, i.e. the liquid portion which comes from cooking of raw shellfish and which is to be discarded as waste, corresponds to the step for taking up edible portion of shellfish by cooking or heat-treating raw shellfish in a hot aqueous solvent or with vapor of such solvent and may therefore be carried out by any method known or conventionally used in the art. Of course, it is important and preferred for the purpose of this invention to control the cooking step so as to yield the desired water-soluble, macromolecular glycoprotein substances having a range of molecular weights within the limits of from 10,000 to 300,000 (hereinafter referred to as "antitumor substances") in as much amount as possible without impairing the primary object for the cooking step. Thus, the following explanation on details of the cooking step will be directed to preferred embodiments for attaining the purpose of this invention.

In order to take up edible portion of shellfish and to recover the liquid portion containing antitumor substances by cooking or heat-treating (hereinafter referred to as "cooking") raw shellfish in a hot aqueous solvent or vapor of such solvent, the cooking operation is effected in one or more steps, in each of which the shellfish is brought into contact with a hot aqueous solvent in the form of liquid and/or vapor which serves as both heating medium and extracting solvent. The method of contact between shellfish and hot aqueous solvent may be selected as desired, for example from among those of direct exposure to solvent vapor, direct pouring of hot solvent and immersion into hot solvent. The hot aqueous solvent may be used in the form of either liquid or vapor or both.

For the purpose of this invention, the raw shellfish may be used in its entirety, i.e. in the shell, or a shelled form with or without liver, as desired. According to this invention, therefore, all the edible portions, i.e. meat, ligament and the like, of shellfish can be used for food after the cooking operation because no cutting or grinding of shellfish is required for cooking.

Usually, the cooking may be carried out at a temperature of about 50°~120° C., preferably about 60°~120° C.

As above-mentioned, the cooking operation may be carried out in one or more, e.g. two or three, steps, the two steps being preferred. In a one-step process, raw shellfish may be treated as desired by subjecting it to exposure to vapor of an aqueous solvent, by pouring a hot aqueous solvent thereon or by immersion thereof into a hot aqueous solvent, whereby to take up all the edible portions of shellfish and to recover the liquid portion from the treated mixture. Typical cooking conditions preferably used for one-step process are given in Table 1. In a two-step process, the first step may follow the one-step process and the second step may preferably be carried out by immersion under heating of the shellfish derived from the first step in a hot aqueous solvent preferably containing sodium chloride whereby to take up all the edible portions of shellfish and to recover the first and second liquid portions from the first and second cooking steps, respectively. Typical cooking conditions preferably used for two-step process are given in Table 2. It will be most preferred for the two-step process to carry out the first step by exposure of raw shellfish to vapor of an aqueous solvent and the second step by immersion of the shellfish thus treated and taken up into a hot aqueoous solvent containing sodium chloride, e.g. in a concentration of 0.2~20% under heating. Such a two-step process is advantageous in that the amount of aqueous solvent to be used is minimized with a high efficiency of extraction of antitumor substances, that the step for concentration of the resulting liquid portion required is simplified and shortened, that the heat efficiency is high and that the apparatus or equipment to be used is less complex.

TABLE 1

Typical cooking conditions for one-step process

| | Embodiment 1 | Embodiment 2 | Embodiment 3 |
|---|---|---|---|
| Starting material | Raw shellfish | Raw shellfish | Raw shellfish |
| Form of aqueous solvent | Hot vapor | Hot liquid | Hot liquid |
| Method of contact between starting material and aqueous solvent | Directly expose starting material to hot vapor | Pour hot liquid to starting material | Heat starting material in hot liquid |
| Temperature of aqueous solvent used °C. | About 100–130 | About 50–100 | About 50–130 |
| (Most preferred temperature) | (About 105–120) | (About 90–100) | (About 90–100) |
| Ratio of aqueous solvent/starting material, wt/wt | About 0.03–0.8 | About 0.05–10 | About 0.6–20 |
| (Most preferred ratio) | (About 0.05–0.5) | (About 0.07–1.0) | (About 1–15) |
| Time of contact between starting material and aqueous solvent, minute | About 3–120 | About 3–120 | About 3–120 |
| (Most preferred time) | (About 5–60) | (About 5–60) | (About 5–60) |
| Cooking temperature, °C. | About 50–120 | About 50–100 | About 50–120 |
| (Most preferred temperature) | (About 60–120) | (About 60–100) | (About 60–100) |

TABLE 2

| | Typical cooking conditions for two-step process | | | |
|---|---|---|---|---|
| | First step | | | |
| | Embodiment 1 | Embodiment 2 | Embodiment 3 | Second step |
| Starting material | Raw shellfish | Raw shellfish | Raw shellfish | Meat portion of shellfish derived from first step |
| Form of aqueous solvent | Hot vapor | Hot liquid | Hot liquid | Hot liquid |
| Method of contact between starting material and aqueous solvent | Directly expose starting material to hot vapor | Pour hot liquid to starting material | Heat starting material in hot liquid | Heat starting material in hot liquid |
| Temperature of aqueous solvent used, °C. | About 100–130 | About 50–100 | About 50–130 | About 50–130 |
| (Most preferred temperature) | (About 105–120) | (About 90–100) | (About 90–100) | (About 90–100) |
| Ratio of aqueous solvent/starting material used, wt/wt | About 0.03–0.8 | About 0.05–10 | About 0.6–20 | About 0.6–20 |
| (Most preferred ratio) | (About 0.05–0.5) | (About 0.07–1.0) | (About 1–15) | (About 1–15) |
| Time of contact between starting material and aqueous solvent, minute | About 3–40 | About 3–40 | About 3–40 | About 3–60 |
| (Most preferred time) | (About 5–20) | (About 5–20) | (About 5–20) | (About 5–30) |
| Cooking temperature, °C. | About 50–120 | About 50–100 | About 50–120 | About 50–120 |
| (Most preferred temperature) | (About 60–120) | (About 60–100) | (About 60–100) | (About 60–100) |

Cooking pressure may be atmospheric, subatmospheric or superatmospheric as desired.

The aqueous solvent to be used for the cooking may include water, saline solution, sea water, aqueous solutions of various water-soluble salts (preferably in a concentration of about 0.5~20% by weight), buffer solutions and aqueous solutions of water-soluble solvents, typically a lower alcohol such as ethanol (preferably in a concentration of about 1~50% by weight), the preferred aqueous solvent being water or saline solution.

The liquid portion coming from the cooking of raw shellfish as above-mentioned, including both the first and second liquid portions in cases of two-step cooking process, which contains antitumor substances may be concentrated to a smaller volume or to dryness to yield a concentrate or dry powder. For this purpose, the liquid portion may be heated at a temperature of about 30°~100° C. under appropriate pressures to concentrate it, treated by dialysis or ultrafiltration to remove salts, or dried by hot-air drying such as spray-drying, or freeze-drying to give dry powder. In cases where the liquid portion is recovered in the form of dry powder in a hot-air dryer, the hot air inlet temperature is usually about 200°~350° C., preferably about 250°~310° C. and the outlet temperature thereof is usually about 80°-170° C., preferably about 100°~150° C. and the contact (residence) time is usually about 5~80 seconds, preferably about 5~50 seconds. Under these conditions, the antitumor substances to be recovered are stable without decomposition.

According to this invention, the concentrate or dry powder thus derived from the liquid portion which comes from the cooking of raw shellfish as waste liquor is treated to isolate antitumor substances which are water-soluble, macromolecular glycoprotein substances having a range of molecular weights within the limits of from 10,000 to 300,000. This may be done by an appropriate combination of various known purification techniques, but we have found a certain specific combination of purification processes which is capable of isolating the desired antitumor substances from the concentrate or dry powder most efficiently and economically.

According to a preferred aspect of this invention, therefore, the treatment for isolating the antitumor substances comprises dissolving the concentrate or dry powder in an aqueous solvent such as water or a buffer solution and subjecting the resulting aqueous solution to a series of chromatographic treatments comprising an ion-exchange chromatography with a basic anion-exchanger and a gel-filtration to collect fractions which are adsorbed on the basic anion-exchanger and which have a range of molecular weights within the limits of from 10,000 to 300,000.

The sequence of the ion-exchange chromatography and gel-filtration may be chosen as desired, but the ion-exchange chromatography followed by gel-filtration is particularly preferred.

Prior to the ion-exchange chromatography or gel-filtration, the aqueous solution of concentrate or dry powder should preferably be pretreated in order to remove insoluble parts and inorganic salts contained therein for assuring a smooth operation of the subsequent treatments.

Thus, according to the most preferred aspect of this invention, the treatment for isolating the antitumor substances comprises dissolving the concentrate or dry powder in an aqueous solvent such as water or a phosphate buffer solution, purifying the resulting aqueous solution from insoluble materials and inorganic salts contained therein, subjecting the resulting aqueous solution to an ion-exchange chromatography with a basic anion-exchanger to adsorb water-soluble, macromolecular glycoprotein substances on the ion-exchanger followed by elution of the substances and subjecting the eluted substances to a gel-filtration to collect fractions having a range of molecular weights within the limits of from 10,000 to 300,000.

The water-soluble glycoprotein substances adsorbed on basic anion-exchanger in an ion-exchange chromatography may be eluted directly with an aqueous sodium chloride solution having a concentration of about 0.07~0.4 M, preferably about 0.1~0.38 M and most preferably about 0.1~0.3 M as eluent.

Details of treatment for isolating the desired antitumor substances from an aqueous solution of the concentrate or dry powder will be given below, in which the evaluation of antitumor activity of the antitumor substances isolated was made by the following method unless otherwise stated.

Thus, ICR mice (female, 6 weeks aged) are inoculated intraperitoneally with Sarcoma 180 tumor cells, followed by withdrawing the reproduced tumor cells together with ascites from the inoculated mice 1 week after the tumor cell inoculation.

0.05 Milliliters (about $4 \times 10^6$ cells) of the 7-day-old Sarcoma 180 ascites tumors so cultured and collected are subcutaneously transplanted into the right groin of female ICR mice, weighing about 23 g. The test samples dissolved in a physiological saline in adequate concentrations (injection volume, 0.1 ml) are injected into the tumor site on days 5, 7, and 9 after tumor inoculation, by which time the tumors have reached an average diameter of 5 mm. At the end of week 5, the mice are killed and the tumors dissected out and weighed. The inhibition ratios are calculated by use of the following formula:

Inhibition ratio (%)=(A−B)/A×100, where A is the average tumor weight of the control group and B is that of the treated group. Complete regression indicates the ratio of the number of mice showing complete tumor regression to the total number of mice tested.

The removal of insoluble materials from the aqueous solution of the concentrate or dry powder may be carried out by any known technique such as centrifuging, filtration and decantation. The removal of inorganic salts from the aqueous solution may also be effected by any known technique such as gel-filtration using a gel capable of fractionating low-molecular weight compounds such as inorganic salts and dialysis through a cellulose membrane against distilled water. In one embodiment useful for the removal of insoluble materials and inorganic salts, the concentrate or dry powder of the liquid portion coming from the cooking of raw shellfish is dissolved in an aqueous solvent such as water or a phosphate buffer solution, preferably a 0.01~0.1 M, more preferably 0.01~0.05 M phosphate buffer solution containing 0~0.15 mol/l of sodium chloride and having a pH of 7.0~7.5 so as to give a concentration of about 10–25% by weight of the concentrate or dry powder on the dry weight basis. A phosphate buffer solution is an aqueous solution of a phosphate mixture of potassium dihydrogenphosphate and disodium hydrogenphosphate. The resulting solution is centrifuged to remove insoluble materials as precipitate and then chromatographed by passing through a column packed with a gel for gel-filtration capable of fractionating substances having molecular weights in the range of about 500~5,000, e.g. Sephadex G-25 (Sephadex is a registered trade mark of Pharmacia Fine Chemicals Co., Uppsala, Sweden) which is a gel obtained by three-dimensionally crosslinking dextran with epichlorohydrin, followed by eluting with the same buffer solution as above so as to collect fractions eluted before the rise in the electric conductivity of the eluate is observed. Thus, the separation of fractions of inorganic salts from those of organic substances may be efficiently achieved. Any other measure is applicable in place of the measure of electric conductivity to determine the boundary for the said separation.

The fractions containing organic substances of relatively high molecular weights thus obtained are then chromatographed by ion-exchange chromatography by passing through a column packed with a basic anion-exchanging gel having a high upper limit of molecular weights to be fractionated, e.g. about 500,000~1,000,000, such as those having diethylaminoethyl or aminoethyl group as an ionizing group. A typical example of such anion-exchanging gel is DEAE-Sepharose CL-6B (Sepharose is a registered trade mark of Pharmacia Fine Chemicals Co.) which is a gel obtained by three-dimensionally crosslinking agarose with 2,3-dibromopropanol followed by introducing diethylaminoethyl group through an ether linkage and which has chloride ion as the counter ion, the upper limit of molecular weights to be fractionated of about $1 \times 10^6$ and the total exchange capacity of $15 \pm 2$ meq/100 ml. Non-adsorbable substances which are mainly composed of polysaccharides and low ion-attractive substances which are eluted with the salt concentration of eluent used are passed through the column without being adsorbed thereon and are therefore removed from adsorbable substances. Then, the substances adsorbed on the gel are eluted with an eluent which is a buffer solution containing sodium chloride, for example a 0.01~0.1 M phosphate buffer solution containing 0.07~0.4 mol/l, preferably 0.1~0.38 mol/l and most preferably 0.1~0.3 mol/l of sodium chloride and having a pH of 7.0~7.5. The fractionation of the eluate at respective ion concentrations is monitored by ultraviolet ray detector and the like.

The NaCl concentrations in the buffer solution used to elute the desired substances in the ion-exchange chromatography above-mentioned are determined on the basis of the result of the following experiment.

The fractions containing organic substances of relatively high molecular weights which were obtained by centrifuging followed by gel-filtration with Sephadex G-25 of the liquid portion which came from the cooking of scallops (*Patinopecten yessoensis*) were freeze-dried. The resulting dry powder (5 g) was dissolved in a 0.01 M phosphate buffer solution (20 ml) having a pH of 7.0, and the resulting solution was passed through a column of DEAE-Sepharose CL-6B equilibrated with a 0.01 M phosphate buffer solution. Chromatographic elution was effected by gradient elution with eluents containing sodium chloride in continuously varying concentrations, giving an elution pattern shown in FIG. 1. Thus, four fractions, A, B, C and D, which were eluted at sodium chloride concentrations of 0, 0~0.1, 0.1~0.25 and 0.25~0.38 mol/l, respectively, were collected.

Figure 1:
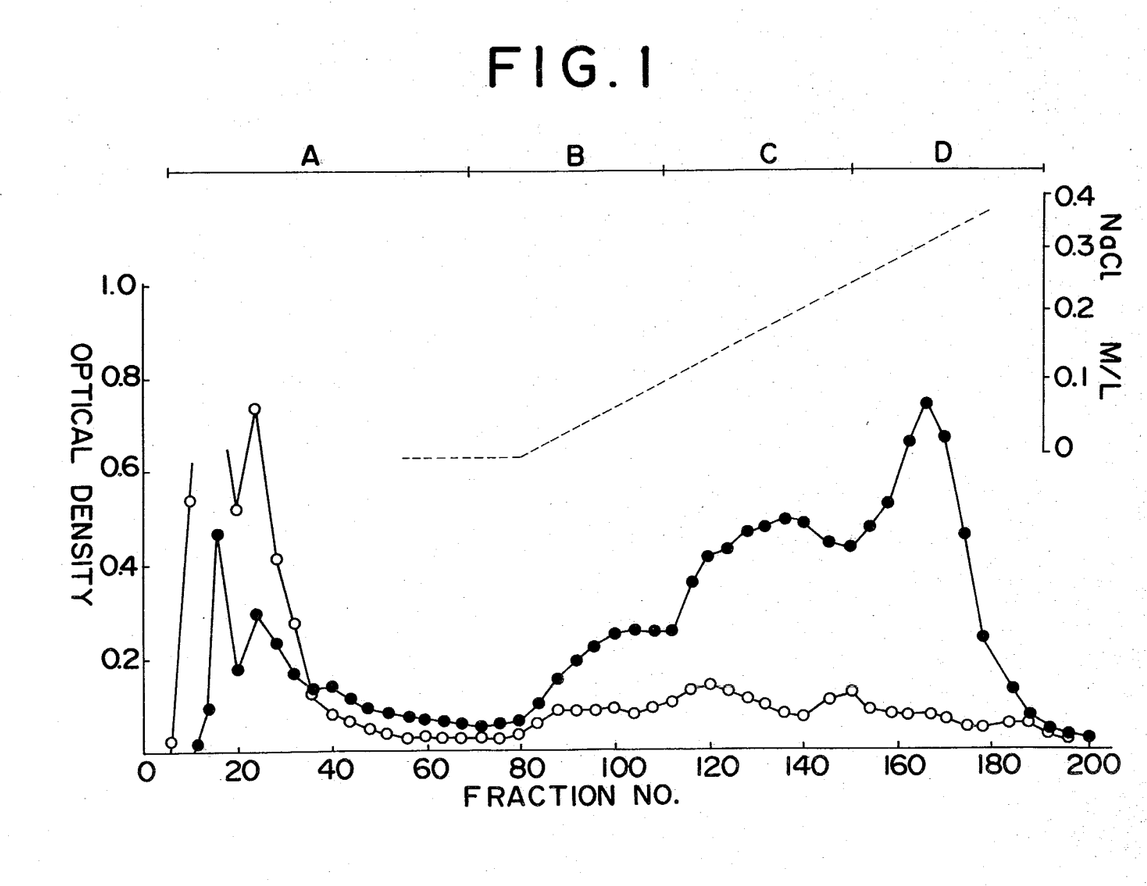

The fractions A, B, C and D so obtained were freeze-dried to form four powders D-A, D-B, D-C and D-D, respectively, and then evaluated for their antitumor activities according to the bioassay method hereinbefore stated in respect of Sarcoma 180 solid tumor. The test results obtained are tabulated in Table 3 below.

TABLE 3

| Test Sample | Dose (mg/mouse × times*) | Average tumor weight (g) | Tumor Inhibition ratio (%) | Complete regression |
|---|---|---|---|---|
| D-A | 10 × 4 | 6.68 | 12.5 | 0/4 |
| D-B | 10 × 4 | 6.22 | 18.5 | 0/3 |
| D-C | 10 × 2<br>5 × 2 | 0.88 | 88.5 | 2/4 |
| D-D | 10 × 2<br>5 × 2 | 2.90 | 62.0 | 1/4 |
| Control | — | 7.63 | — | 0/4 |

(Note)
*times: 5, 7, 9 and 11 days after the tumor transplantation.

The above results indicate that the freeze-dried powder (D-C) obtained from fraction C eluted from DEAE-Sepharose column with 0.01 M phosphate buffer solutions containing 0.1 M~0.25 M sodium chloride has a strong antitumor activity among the samples (D-A), (D-B) and (D-D), as it gave a 88.5% tumor inhibition ratio with complete regression in 2 of 4 mice tested.

Figure 2:
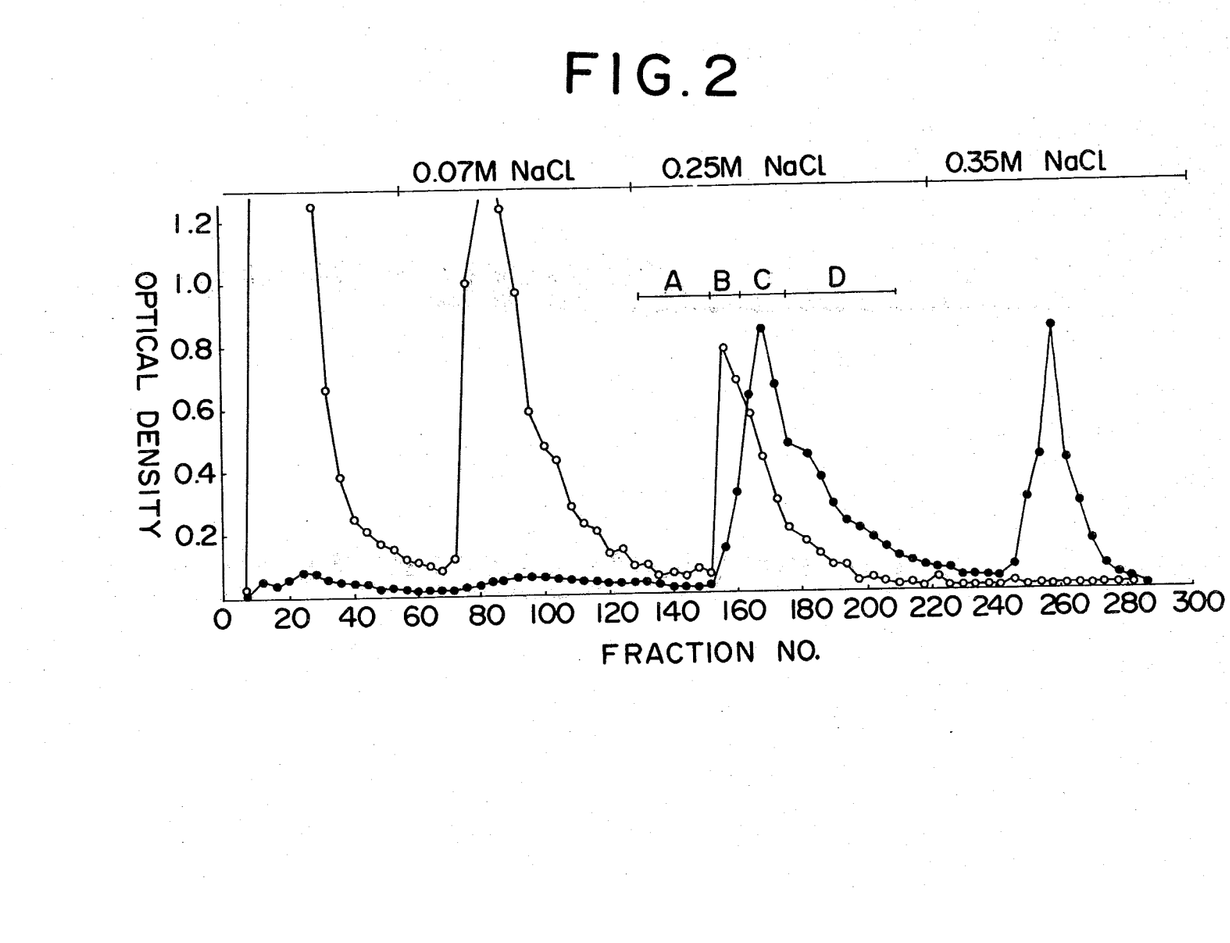

Further, the same fractions as used in the preceding ion-exchange chromatographic operation, i.e. the fractions containing organic substances which were obtained by centrifuging followed by gel-filtration of the liquid portion which came from the cooling of scallops were dissolved in a volume of a 0.01 M phosphate buffer solution (pH 7.5), followed by chromatography in a column of DEAE-Sepharose CL-6B developed with 0.01 M phosphate buffer solutions (pH 7.5) containing different concentrations of sodium chloride, with the sodium chloride concentration being stepwise changed from 0.07 M to 0.25 M to 0.35 M, and with the eluate being collected in 15 ml-fractions. The elution pattern obtained in this chromatography is shown in FIG. 2. Further, the fractions eluted with 0.01 M phosphate buffer solution containing 0.25 M sodium chloride were sub-divided into four fractions, so that the fractions Nos. 130~152 where no absorption peak was observed were combined together as fraction A; the fractions Nos. 153~162 where the absorption peak of carbohydrates was observed were combined together as fraction B; the fractions Nos. 163~176 where the absorption peak of proteins was observed were combined together as fraction C; and the last fractions Nos. 177~210 were combined together as fraction D. These fractions A, B, C and D were freeze-dried to form four powders DS-A, DS-B, DS-C and DS-D, respectively, and then evaluated for their antitumor activities against Sarcoma 180 solid tumor according to the bioassay method stated hereinbefore. The test results obtained are shown in Table 4 below.

TABLE 4

| Test Sample | Dose (mg/mouse × times) | Average tumor weight (g) | Tumor Inhibition ratio (%) | Complete regression |
|---|---|---|---|---|
| DS-A | 10 × 3 | 2.79 | 72.8 | 0/6 |
| DS-B | 10 × 3 | 2.96 | 71.2 | 0/6 |
| DS-C | 10 × 3 | 2.07 | 79.8 | ⅛ |
| DS-D | 10 × 3 | 6.66 | 35.1 | 0/5 |
| Control | — | 10.26 | — | 0/7 |

From the above results, it is seen that fraction DS-D showed a weak antitumor activity, while fractions DS-A, DS-B and DS-C showed marked antitumor activities.

The above experiments indicate that when the DEAE-Sepharose column was eluted with a phosphate buffer solution (pH 7.5) containing about 0.07~0.4 M sodium chloride, the desired antitumor-active substances were concentrated effectively.

The aqueous solution containing the desired substances thus obtained by the ion-exchange chromatography is then subjected to gel-filtration to isolate those substances having a range of molecular weights within the limits of from 10,000 to 300,000. For this purpose, the aqueous solution is previously treated for the removal of inorganic salts and for the concentration to a smaller volume or to dryness. The removal of inorganic salts or desalting may be carried out in the similar manner as above, for example by gel-filtration of dialysis.

One typical embodiment of the pretreatment at this stage comprises concentrating the aqueous solution at a temperature below 40° C., preferably below 20° C., under a reduced pressure to about 1/5~1/6 volume, passing the concentrated solution through a column of gel for gel-filtration capable of fractionating substances having molecular weights of about 500~5,000, e.g. Sephadex G-25, eluting the column with distilled or deionized water to separate fractions containing inorganic salts from those containing desired organic substances by monitoring the electric conductivity of eluate fractions, concentrating the fractions containing desired organic substances at a temperature below 40° C., preferably below 20° C. under a reduced pressure to about 1/5~1/6 volume and freeze-drying the concentrate to form dry powder. The yield of the dry powder is about 1/60~1/100 based on the concentrate or the dry powder obtained from the liquid portion which comes from the cooking of raw shellfish.

Figure 3:
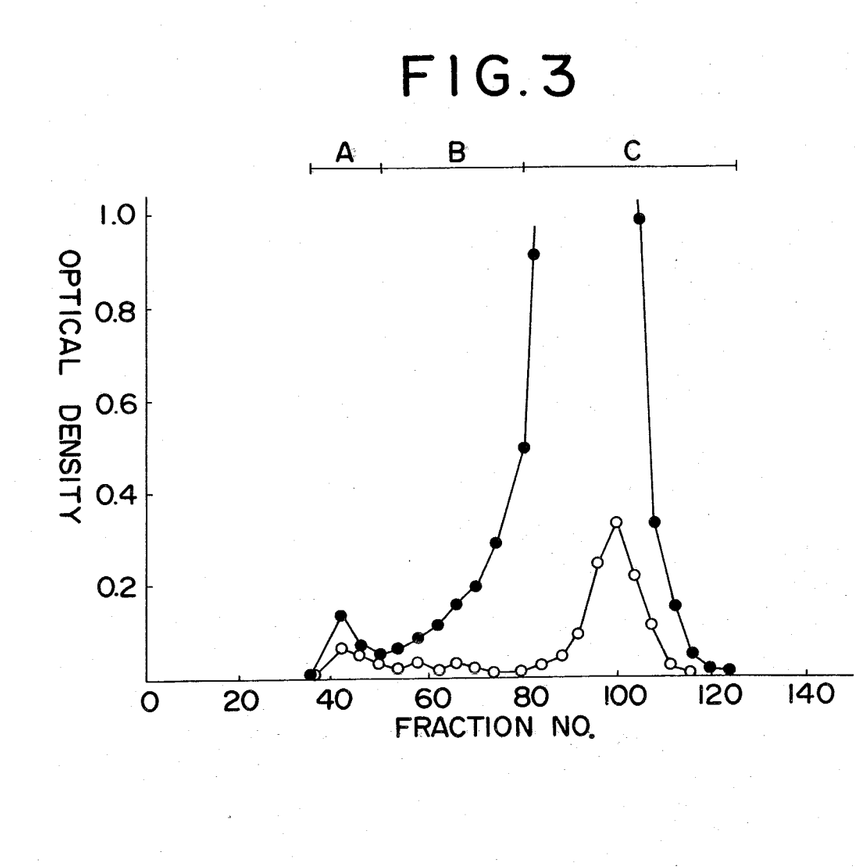
FIG. 3 shows an elution pattern depicted on elution with phosphate buffer solutions in gel-filtration of the fraction C of FIG. 1 using a gel having a fractionation range of molecular weights of 1,500~100,000, wherein abscissa and ordinate axes and the white and black circles represent same meanings as those given in the preceding figures.

The subsequent gel-filtration for the isolation of desired organic substances having a desired range of molecular weights is preferably carried out by using a gel capable of fractionating substances having molecular weights of 1,500~100,000, e.g. Sephadex G-75 (Sephadex is a registered trade mark of Pharmacia Fine Chemicals Co.) which is a gel obtained by three-dimensionally crosslinking dextran with epichlorohydrin. According to one typical embodiment of this gel-filtration step, 1 g of the dry powder which is obtained by desalting and freeze-drying fraction D-C derived from elution in the ion-exchange chromatography is dissolved in 5 ml of a 0~0.1 M phosphate buffer solution having a pH of 7.0~7.5. The resulting solution is passed through a column of Sephadex G-75 which has been equilibrated with a 0~0.1 M phosphate buffer solution having a pH of 7.0~7.5. The column is then eluted with a 0~0.1 M phosphate buffer solution having a pH of 7.0~7.5 as eluent. One example of elution patterns given in such gel-filtration is shown in FIG. 3. Thus, three fractions A, B and C were collected, the initial fraction A showing small peaks of protein and carbohydrates, the middle fraction B showing little or no peak of carbohydrates, but containing a substantial amount of protein and the final fraction C showing strong peaks of protein and carbohydrates. Fractions A, B and C so obtained were then dialyzed against water for the de-salting purpose and then freeze-dried to give the three powders G-A, G-B and G-C, respectively.

These powders G-A, G-B and G-C were examined for their antitumor activity against Sarcoma 180 solid tumor by the bioassay method hereinbefore stated. The results obtained are shown in Table 5 below.

TABLE 5

| Test Sample | Dose (mg/mouse × times) | Average tumor weight (g) | Tumor Inhibition ratio (%) | Complete regression |
|---|---|---|---|---|
| G-A | 2 × 3 | 1.79 | 73.9 | 1/6 |
| G-B | 2 × 3 | 3.21 | 57.5 | 0/4 |
| G-C | 2 × 3 | 3.72 | 50.5 | 0/5 |
| Control | — | 7.55 | 0 | 0/6 |

It is observed that powder G-A showed the highest antitumor potency among the other powders G-B and G-C and could be recovered in the highest yield (usually of about 2% based on the weight of the crude powder recovered from the ion-exchange chromatography step), revealing that the gel-filtration of crude powder of the active substances with Sephadex G-75 column could afford the highest efficiency in the purification of the active substances.

To estimate approximately how much was the lower limit of the molecular weights of the glycoprotein substances present in the above-mentioned powder G-A, this powder was subjected to gel-filtration with Sephadex G-50 (a product of Pharmacia Fine Chemicals Co.) with reference to the molecular weights of tryptophane, vitamin $B_{12}$, cytochrome C and ovalbumin, when it was found that powder G-A comprised glycoprotein substances having molecular weights of not less than about 10,000. Thus, when a crude powder of the active substances recovered from the preceding stage of the anion-exchange chromatography is further purified by gel-filtration using a gel capable of fractionating substances having molecular weights of 1500~100,000, e.g. Sephadex G-75 to obtain the active glycoprotein substances having molecular weights of not less than 10,000, it is found that said crude powder can be purified in an industrial large scale, and be purified efficiently without causing deactivation of the active substances.

Powder G-A obtained above is further purified by the following procedure.

One gram of powder G-A is dissolved in a small amount of a 0~0.1 M phosphate buffer solution having a pH of 7.0~7.5 and the resulting solution is passed through a column packed with a gel for gel-filtration capable of fractionating substances having molecular weights of 10,000~2,000,000 which has been equilibrated with a 0~0.1 M phosphate buffer solution having a pH of 7.0~7.5, e.g. Sephacryl S-400 (Sephacryl is a registered trade mark of Pharmacia Fine Chemicals Co.) which is one obtained by crosslinking allyldextran with N,N'-methylenebisacrylamide. Elution is effected with a 0~0.1 M phosphate buffer solution having a pH of 7.0~7.5 to yield fraction A corresponding to molecular weights higher than 300,000, fraction B corresponding to molecular weights ranging 300,000~150,000 and fraction C corresponding to molecular weights lower than 150,000. Each of the three fractions A, B and C is recovered in the form of dry powder S-A, S-B and S-C, respectively, by subsequent dialysis and freeze-drying.

The purified glycoprotein powders (S-A), (S-B) and (S-C) so obtained as in Example 4 were examined for their antitumor activity against Sarcoma 180 solid tumor by the bioassay method as stated hereinbefore. The test results obtained are shown in Table 6 below.

TABLE 6

| Test Sample | Dose (mg/mouse × times) | Average wt. of tumors (g) | Inhibition ratio (%) | Complete regression |
|---|---|---|---|---|
| S-A | 1 × 3 | 5.38 | 40.5 | 0/5 |
| S-B | 1 × 3 | 2.25 | 75.1 | 1/5 |
| S-C | 1 × 3 | 2.27 | 74.9 | 1/5 |
| Control | — | 9.05 | — | 0/8 |

From the above table, it is seen that powder (S-A) comprising the glycoprotein substances of higher than 300,000 in molecular weight showed a weaker antitumor activity than that of powder (S-B) comprising the glycoprotein substances of 150,000~300,000 in molecular weight, as well as of powder (S-C) comprising the glycoprotein substances of 10,000~150,000 in molecular weight, and also that powder (S-B) was not significantly different from powder (S-C) in the degree of their antitumor activity.

We have made comparison in physical and chemical properties of the antitumor agent consisting essentially of water-soluble, macromolecular glycoprotein substances according to this invention as typified by those given later in Example 5 with known similar antitumor agents derived from shellfish which are disclosed in Japanese Patent Publication No. 8088/82, Japanese Patent KOKAI Nos. 41314/79 and 41315/79 and Journal of National Cancer Institute, Vol. 60, No. 6, 1499~1500, June 1978 by T. Sasaki et al. and found no similarity which makes it possible to identify the antitumor agent of this invention with those disclosed in literature. We believe therefore that the antitumor agent according to this invention is a new composition.

The antitumor agent according to this invention may be used in combination with one or more other antitumor agents, if desired. Particularly effective is a combination with other antitumor agent which will enhance the immunopotenciating effect. The antitumor agent according to this invention has such particular advantages that it has a broad antitumor spectrum without appreciable cytotoxicity and that a noticeable tumor regression effect can be achieved by adopting various administration routes including intravenous, intraperitoneal, intracutaneous, subcutaneous, and intratumoral administrations.

Characteristic features and advantages of the process for the preparation of antitumor agent according to this invention are summarily given below.

Firstly, the process of this invention is characterized in that it utilizes as starting material the liquid portion which comes from the cooking of raw shellfish for the purpose of obtaining edible portions thereof and which is usually discharged as waste, from which the desired antitumor substances can be efficiently recovered. This is based on our discovery that the desired antitumor agent which consists essentially of water-soluble, macromolecular glycoprotein substances having a range of molecular weights within the limits of from 10,000 to 300,000 can be recovered from shellfish through a high temperature treatment thereof without impairing the antitumor activity of the desired antitumor agent and without affecting edible portions of the shellfish. Such a discovery is surprising in view of the prior art teaching that extraction of antitumor substances from shellfish should be carried out at a low temperature, i.e. without heating, to avoid any deterioration of the desired substances.

Secondly, the process of this invention is much more simple and inexpensive than the processes hitherto proposed as disclosed in the Japanese patent publication and KOKAI publications above-referred to. In the prior art processes, edible portions of raw shellfish must be used as starting material and the extraction thereof at a low temperature requires such troublesome treatments as removal of liver from edible portions of shellfish, cutting of the edible portions into fine pieces, homogenization of the fine pieces to serve efficient extraction, e.g. by sonication, and removal of the consumed mass after extraction, e.g. by centrifuging. A further disadvantage of the low-temperature extraction of the prior art is that the resulting extract contains not only the desired antitumor substances but also many other substances, particularly macromolecular organic substances, thus making the purification steps required more complex. In contrast, the process of this invention does not require any step for extraction and subsidiaries thereto but may utilize the liquid portion which comes from cooking of raw shellfish for recovery of edible portions thereof and which is usually discarded as waste. The liquid portion from the cooking step of raw shellfish contains other substances than the desired antitumor substances, particularly other organic macromolecular substances in relatively low proportions in comparison with the extract in the prior art processes and is therefore purified more easily for the recovery and isolation of the desired antitumor substances therefrom.

The process of this invention is also advantageous in view of environmental protection in that a substantial amount of organic substances contained in the liquid portion coming from cooking of raw shellfish can be recovered as useful product with the result that the organic contents of the waste liquor are substantially reduced.

This invention is now illustrated with reference to the following Examples to which the invention is limited in no way.

EXAMPLE 1

One part (by weight) of raw scallop shellfish (*Patinopecten yessiensis*) in the shells was charged into a vessel continuously, into which 0.10 parts (by weight) of superheated steam at 105°~110° C. was blown so that the raw scallop shellfish was directly exposed to the blown steam and steamed at 90°~100° C. for 10 minutes. At the bottom of the vessel, there was collected a volume of the water condensate which was usually such one to be discarded as waste liquor in the conventional cooking process of scallops but which was now recovered according to this invention as a first crop solution of the active substances. The outer shells of raw scallop shellfish used as the starting material had about 0.1 parts (by weight) of the infesting acorn shells attached thereto. The first crop solution of the active substances was removed out of said vessel and then slowly cooled down from 90° C. to 50° C. and then immediately passed into a spraying drier. This drier had an inlet for hot air through which a stream of hot air at 280° C. was passed into the drier, as well as an outlet for effluent gases through which the effluent gases were discharged from the drier at a temperature of 125° C. or higher. The first crop solution of the active substances which was passed into the spraying drier was finely divided into a spray within said drier and dried into powder in a retention time of 45 seconds, and the resulting dried powder was carried along with the effluent gases out of the spraying drier and collected by a collector. In this way, a first crude powder of the active substances was obtained in a yield of 0.27% by weight based on the whole weight of the raw scallop shellfish employed.

Then, the shell-ligament portions were removed from the shellfish by means of knife. The scallop ligament so collected (50 kg) was placed into a volume (450 kg) of a boiling solution containing 10% by weight of sodium chloride in water and then boiled in the boiling saline water for 20 minutes. With the same saline water, further three 50 kg portions of the scallop ligament were treated for the boiling process. This saline water was recovered as a second crop solution of the active substances. The steamed meat portions and the boiled ligament portions of the scallops were then frozen for sale and use. The second crop solution of the active substances as recovered was slowly cooled down from 90° C. to 40° C. and processed in the same manner as for the first crop solution of the active substances by means of the spraying drier to give a second crude powder of the active substances in a yield of 0.20% by weight based on the whole weight of the scallop shellfish employed.

Two parts by weight of the first crude powder of the active substances were admixed with one part by weight of the second crude powder of the active substances to give a third crude powder of the active substances.

EXAMPLE 2

The third crude powder (600 g) obtained in Example 1 was admixed with 3 kg of distilled water, and the resulting aqueous suspension was centrifuged at 10,000 G for 20 minutes at 5° C. to remove the insoluble parts therefrom. The supernatant solution obtained (3 liters) was passed for the desalting purpose into a column of 16 l of a gel-filtration gel, Sephadex G-25 (a product of Pharmacia Fine Chemicals Co.) which had been swollen with water and then had been equilibrated with a 0.01 M phosphate buffer solution (pH 7.5) containing 0.07 mol/liter of sodium chloride. This column was subsequently eluted with a further volume of the same 0.01 M phosphate buffer solution (pH 7.5) containing 0.07 mol/liter of sodium chloride. The electroconductivity of the eluate was measured continuously, and the fractions which showed low electroconductivity were collected. Such fractions containing the sodium chloride eluted out showed a higher electric conductivity, whereas such fractions containing the active substances but containing no sodium chloride showed a lower electric conductivity. The fractions of the lower electric conductivity were combined together and passed through a column of 16 l of an ion-exchanging gel, DEAE-Sepharose CL-6B which had been equilibrated with a 0.01 M phosphate buffer solution (pH 7.5) containing 0.07 mol/liter of sodium chloride, for the purpose of separating off the undesirable substances such as polysaccharides and substances having low ion-affinity. The effluent firstly running through the DEAE-Sepharose column was discarded. After it was confirmed by means of an ultra-violet ray monitor that the effluent did no longer run out of the column, the column having adsorbed the active substances was then eluted with a volume of a 0.01 M phosphate buffer solution (pH 7.5) containing 0.25 mol/liter of sodium chloride. The eluate from the column was collected and the fractions so obtained containing the active substances were combined together and dialyzed against deionized water at 5° C. for two days for the de-salting purpose.

The active fraction so dialyzed was then freeze-dried to give 7.2 g of a fourth powder which was effective against Sarcoma 180 in ICR mice, with a dose of 400 mg/kg intratumorally given once a day for 3 days. This powder also showed a pronounced antitumor effect against Meth-A in BALB/c mice with a dose of 400 mg/kg intratumorally given once a day for 6 days; it showed a 100% inhibition ratio with complete tumor regression in 6 of 6 mice tested.

EXAMPLE 3

For the purpose of further purifying, the fourth crude powder (30 g) obtained from repetition of the procedure of Example 2 was dissolved in 150 ml of a 0.1 M phosphate buffer solution (pH 7.5), and the resulting solution was charged into a column (90 cm height × 14 cm diameter) of a gel-filtration gel, Sephadex G75 which had been equilibrated with another volume of the same 0.1 M phosphate buffer solution (pH 7.5). The Sephadex G75 column having adsorbed the active substances was then eluted with a further volume of the same 0.1 M phosphate buffer solution (pH 7.5). The eluate was collected in 15 ml-fractions. The active fractions which were containing the active substances having molecular weights of not less than 10,000 were combined together and dialyzed against deionized water at 5° C. for 48 hours for the desalting. The active fraction so dialyzed was then freeze-dried to give 0.8 g of a fifth crude powder which showed a strong antitumor activity (80.5% inhibition ratio) against Sarcoma 180 solid tumor with a dose of 40 mg/kg for 3 days.

EXAMPLE 4

For further purification and fractionation of the fifth crude powder, the fifth crude powder (1.0 g) obtained from repetition of the procedure of Example 3 was dissolved in 10 ml of a 0.01 M phosphate buffer solution (pH 7.5) and the resulting solution was chromatographed in a column (50 cm height × 2.5 cm diameter) of a gel-filtration gel, Sephacryl S-400 (a product of Pharmacia Fine Chemicals Co.) which had been well equilibrated with another volume of the same 0.01 M phosphate buffer solution (pH 7.5). The elution of this Sephacryl S-400 column was effected with a further volume of the same 0.01 M phosphate buffer solution (pH 7.5) while the eluate was collected in 15 ml-fractions. The fractions No. 28 to No. 40 were combined together as the first glycoprotein fraction (A) containing the active substances of molecular weights of higher than 300,000; the fractions Nos. 41 to No. 65 were combined together as the second glycoprotein fraction (B) containing the active substances of molecular weights of from 150,000 to 300,000; and the fractions No. 66 to No. 95 were combined together as the third glycoprotein fraction (C) containing the active substances of molecular weights of less than 150,000 but not less than 10,000. The fractions (A), (B) and (C) were each dialyzed against distilled water for 48 hours and then freeze-dried to give 0.18 g of a purified glycoprotein powder (S-A), 0.35 g of a purified glycoprotein powder (S-B) and 0.30 g of a purified glycoprotein powder (S-C), respectively.

These glycoprotein powders (S-A), (S-B) and (S-C) were estimated for their antitumor activity against Sarcoma 180 solid tumor, when it was revealed that the second glycoprotein powder (S-B) had a significant antitumor activity against Sarcoma 180 solid tumor which was substantially as high as that of the third glycoprotein powder (S-C) and which was higher than the anti-tumor potency of the fifth crude powder of the active substances as obtained in Example 3, and also that the first glycoprotein powder (S-A) showed no significant antitumor activity against Sarcoma 180 solid tumor.

EXAMPLE 5

Figure 4:
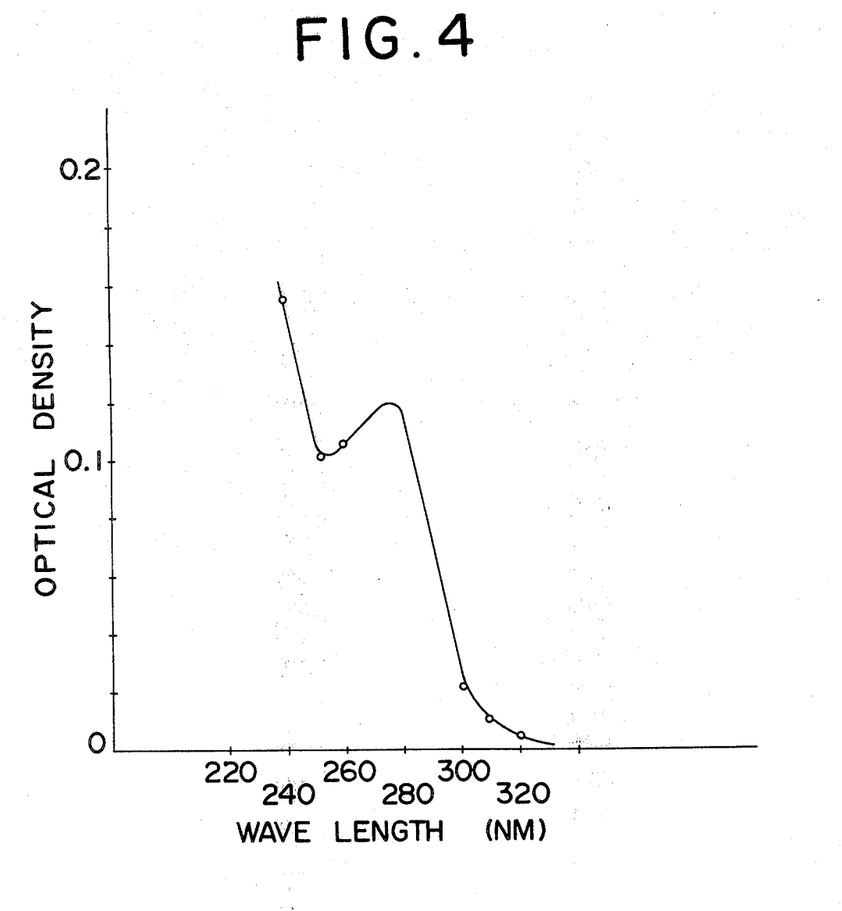
FIGS. 4 and 5 show ultraviolet absorption spectrum and infrared absorption spectrum, respectively, of water-soluble glycoprotein substances having a range of molecular weights of 10,000~300,000 which were obtained by gel-filtration of the fraction C in FIG. 1 followed by another gel-filtration to remove fractions having molecular weights higher than 300,000.
Figure 5:
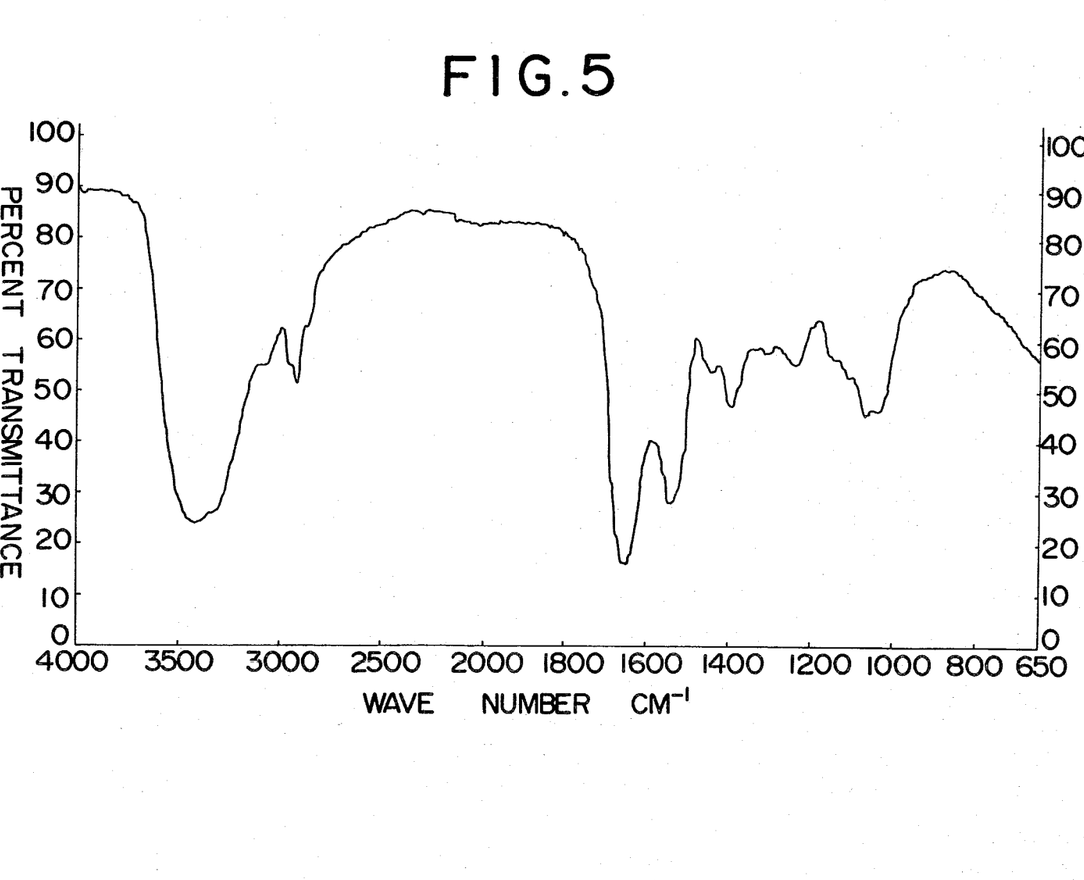

The mixed powder of the active glycoprotein powders (S-B, 210 mg) and (S-C, 180 mg) of Example 4 was dissolved in a volume of distilled water, followed by freeze-drying to afford 0.39 g of a sample powder (S-D) of the active glycoprotein. This sample powder (S-D) of the active glycoprotein obtained according to this invention showed the following physico-chemical properties:

| | | |
|---|---|---|
| (1) | Elemental analysis: | C 43.2%, H 6.5%, N 10.1%, P 0.12% S 0.1%, ash 1% by weight. |
| (2) | Molecular weight: | About 10,000 to about 300,000 as measured by gel-filtration chromatography. |
| (3) | Melting point: | No definite melting point with decomposing at 235° C. |
| (4) | Specific optical rotation: | $[\alpha]_D^{20} - 15.7°$ (c = 0.5% by wt. in water) |
| (5) | Ultraviolet absorption spectrum: | A solution of 0.4 mg of the sample powder per ml of water gave the UV absorption spectrum as shown in FIG. 4, with a characteristic absorption peak $\lambda_{max}^{H2O}$ at 278 nm. |
| (6) | Infrared absorption spectrum (pelleted in KBr): | As shown in FIG. 5, with characteristic absorption peaks at 3500–3300, 1650, 1540 and 1400 cm$^{-1}$. |
| (7) | Solubility: | Soluble easily in water but insoluble in organic solvents such as methanol, ethanol and acetone. |
| (8) | Color reactions: | Positive in biuret reaction, xanthoproteic reaction, phenolic reagent reaction, anthrone-sulfuric acid reaction and phenol-sulfuric acid reaction; but pseudo-positive in cysteine-sulfuric acid reaction. |
| (9) | Acidic or basic nature: | Amphoteric electrolyte. |
| (10) | Substance color and appearance: | White-colored solid with or without faint brown tinge. |
| (11) | Amino acids in hydrolysate: | When hydrolyzed in 6N HCl at 105–110° C. for 24 hours, the resulting hydrolysate contains at least the following amino acids:- aspartic acid, hydroproline, threonine, serine, glutamic acid, proline, glycine, alanine, cysteine, valine, methionine, isoleucine, leucine, tyrosine, phenylalanine, lysine, arginine, histidine, hydroxylysine. |
| (12) | Carbohydrates in hydrolysate: | When hydrolyzed in 2N HCl at 80–90° C. for 10 hours, followed by the removal of the amino acids from the hydrolysate by ion-exchange chromatography and further by hydrogenation of the amino acids-free hydrolysate, the hydrogenated hydrolysate contains at least the following carbohydrates: fructose, mannose, fucose, inositol, galactose. |
| (13) | Protein content: | The protein content amounts to 60.5% by weight in terms of fatal bovine serum albumin when measured |

| | -continued |
|---|---|
| (14) Carbohydrate content: | by Lowry-Folin method with coloration by phenolic reagent. The carbohydrate content amounts to 19.9% by weight in terms of glucose when measured by the phenol-sulfuric acid method. |
| (15) Nucleic acid content: | The nucleic acid content amounts to 0.8% or less by weight in terms of adenylic acid when measured according to the diphenylamine method by Dische reaction. |

Further, to evaluate the biological properties of sample powder (S-D) of this invention, the antitumor effect of sample powder (S-D) on Sarcoma 180 solid tumor was determined by the bioassay method hereinbefore stated, by injecting an aqueous solution of said sample powder directly into the tumor site at various dosages three times, namely on days of 5, 7 and 9 after the tumor inoculation in ICR mice. The test results obtained are tabulated in the following table.

TABLE 7

| Test Sample | Dosage (mg/mouse × times) | Average wt. of tumor (g) | Inhibition ratio (%) | Complete regression |
|---|---|---|---|---|
| S-D | 2 × 3 | 1.97 | 73.9 | 1/6 |
| S-D | 1 × 3 | 1.61 | 78.1 | 1/5 |
| S-D | 0.5 × 3 | 0.05 | 99.3 | 3/4 |
| S-D | 0.2 × 3 | 3.40 | 66.9 | 1/3 |
| S-D | 0.1 × 3 | 4.55 | 38.1 | 0/5 |
| Control (untreated) | | 7.55 | 0 | 0/8 |

Administration by various routes such as intravenous, intraperitoneal and subcutaneous injections of sample powder (S-D) at various dosages (0.5~5 mg/mouse×1~3 times) in Sarcoma 180 solid tumor-bearing ICR mice also exhibited a significant antitumor activity (50%~91% in inhibition ratios).

Furthermore, to examine any direct cytocidal effect of the water-soluble glycoprotein substances of this invention on tumor cell, mouse Lymphoma L 5178 Y cells were cultured at the concentration of 5×10⁵ cells/ml in RPMI medium 1640 containing glycoprotein powder (S-B) or (S-C) of Example 4 or sample powder (S-D) of this Example 5 at concentrations of 40 to 200 mg/ml. After culturing at 37° C. for 48 hours, the viability of the tumor cells was examined by trypan blue staining, when it was observed that the tumor cells showed 100% viability, revealing that glycoprotein powders (S-B), (S-C) and (S-D) had no direct cytocidal effect on the tumor cell.

EXAMPLE 6

This Example illustrates the antitumor activity of the water-soluble glycoprotein substances of this invention on the other tumors than Sarcoma 180 solid tumor.

The tumor cells (4×10⁶ cells/mouse) of Ehrlich carcinoma, Leukemia SN-36, NTF reticulum cell sarcoma or Meth/A Fibrosarcoma were subcutaneously injected into the inguinal part of ICR mice or BALB/c mice (6 weeks aged). One week after the tumor cell inoculation, the tumor cells had grown to solid tumors. A solution in physiological saline of sample powder (S-D) obtained in Example 5 was injected into the tumor site at a unit dosage of 5 mg/mouse three times, namely on days 5, 7 and 9 after the tumor cell inoculation. Five weeks after the tumor cell inoculation, the mice were sacrificed and the tumors dissected out and weighed. The inhibition ratio (%) was calculated as compared with the control groups of mice which received the tumor cell inoculation and injection of physiological saline water containing no test sample.

The test results obtained are summarized in Table 8 below.

TABLE 8

| | Inhibition ratio (%) | | | |
|---|---|---|---|---|
| Test substance (Mice tested) | Ehrlich carcinoma (ICR mice) | Leukemia SN-36 (ICR mice) | NTF reticulum cell sarcoma (ICR mice) | Meth/A Fibrosarcoma (BALB/c mice) |
| S-D | 80.3 | 95.5 | 83.5 | 90.2 |
| Control | 0 | 0 | 0 | 0 |

EXAMPLE 7

Raw horned turban shellfish (*Batillus cornutus*) in their shells was steamed and boiled in the same manner as in Example 1. The water condensate collected was spray-dried in the same manner as in Example 1. The resulting dried powder was processed with Sephadex G-25 and with DEAE-Sepharose CL-6B in the same manner as in Example 2, then with Sephadex G75 in the same manner as in Example 3 and with Sephacryl S-400 in the same manner as in Example 4, and then blended in the same manner as in Example 5 to give a white-colored powder of water-soluble glycoproteins having molecular weights of from 10,000 to 300,000 as measured by the gel-filtration chromatography. This purified glycoprotein powder showed a significant antitumor activity as it gave 65% inhibition ratio against Sarcoma 180 solid tumor when tested by the bioassay method stated hereinbefore at a dosage of 400 mg/kg×3 times.

EXAMPLE 8

Raw abalone shellfish (*Haliotis discus*) in their shells was steamed and boiled in the same manner as in Example 1. The water condensate collected was spray-dried in the same manner as in Example 1. The resulting dried powder was processed with Sephadex G-25 and with DEAE-Sepharose CL-6B in the same manner as in Example 2, then with Sephadex G75 in the same manner as in Example 3 and with Sephacryl S-400 in the same manner as in Example 4, and then blended in the same manner as in Example 5 to give a white-colored powder of water-soluble glycoproteins having molecular weights of from 10,000 to 300,000 as measured by the gel-filtration chromatography. This purified glycoprotein powder showed a significant antitumor activity as it gave 73% inhibition ratio against Sarcoma 180 solid tumor when tested by the bioassay method stated hereinbefore at a dosage of 400 mg/kg×3 times.

EXAMPLE 9

Raw Asian hard clam shellfish (*Meretrix lusoria*) in their shells was steamed and boiled in the same manner as in Example 1. The water condensate collected was spray-dried in the same manner as in Example 1. The resulting dried powder was processed with Sephadex G-25 and with DEAE-Sepharose CL-6B in the same manner as in Example 2, then with Sephadex G75 in the same manner as in Example 3 and with Sephacryl S-400 in the same manner as in Example 4, and then blended in the same manner as in Example 5 to give a white-colored powder of water-soluble glycoproteins having molecular weights of from 10,000 to 300,000 as measured by the gel-filtration chromatography. This purified glycoprotein powder showed a significant antitumor activity as it gave 67% inhibition ratio against Sarcoma 180 solid tumor when tested by the bioassay method stated hereinbefore at a dosage of 400 mg/kg×3 times.

EXAMPLE 10

The procedures of Examples 2, 3, 4 and 5 were repeated using the first crude powder of the active substances obtained in Example 1 (by spray-drying the first crop solution of the active substances, namely the water-condensate recovered from the steaming of scallops) in place of the third crude powder of the active substances of Example 1. There was afforded a white-colored powder of water-soluble glycoproteins which exhibited the physico-chemical properties substantially the same as those of sample powder (S-D) of Example 5 and also gave an antitumor activity against Sarcoma 180 solid tumor as high as that of sample powder (S-D) of Example 5.

EXAMPLE 11

The procedures of Examples 2, 3, 4 and 5 were repeated using the second crude powder of the active substances obtained in Example 1 (by spray-drying the second crop solution of the active substances as recovered from the boiling of the scallop ligaments with saline water) in place of the third crude powder of the active substances of Example 1. There was afforded a white-colored powder of water-soluble glycoproteins which exhibited the physico-chemical properties substantially the same as those of sample powder (S-D) of Example 5 and also gave an antitumor activity against Sarcoma 180 solid tumor as high as that of sample powder (S-D) of Example 5.

What we claim is:

1. A process for the preparation of an antitumor agent consisting essentially of water-soluble, macromolecular glycoprotein substances having a range of molecular weights within the limits of from 10,000 to 300,000 from shellfish which comprises recovering the liquid portion which comes from cooking of raw shellfish in a hot aqueous solvent or with vapor of such solvent and which is to be discarded as waste, concentrating the liquid portion thus recovered to a smaller volume or to dryness to yield a concentrate or dry powder and isolating the water-soluble, macromolecular glycoprotein substances from the concentrate or dry powder.

2. A process for the preparation of an antitumor agent consisting essentially of water-soluble macromolecular glycoprotein substances having a range of molecular weights within the limits of from 10,000 to 300,000 from shellfish which comprises recovering the liquid portion which comes from cooking of raw shellfish in a hot aqueous solvent or with vapor of such solvent and which is to be discarded as waste, concentrating the liquid portion thus recovered to a smaller volume or to dryness to yield a concentrate or dry powder, dissolving the concentrate or dry powder in an aqueous solvent and subjecting the resulting aqueous solution to a series of treatments comprising an ion-exchange chromatography with a basic anion-exchanger and a gel-filtration whereby to collect fractions which are adsorbed on the basic anion-exchanger and which have a range of molecular weights within the limits of from 10,000 to 300,000.

3. A process for the preparation of an antitumor agent consisting essentially of water-soluble, macromolecular glycoprotein substances having a range of molecular weights within the limits of from 10,000 to 300,000 from shellfish which comprises recovering the liquid portion which comes from cooking of raw shellfish in a hot aqueous solvent or with vapor of such solvent and which is to be discarded as waste, concentrating the liquid portion thus recovered to a smaller volume or to dryness to yield a concentrate or dry powder, dissolving the concentrate or dry powder in an aqueous solvent, subjecting the resulting aqueous solution to an ion-exchange chromatography with a basic anion-exchanger to adsorb water-soluble macromolecular glycoprotein substances on the exchanger followed by desorption of the substances and subjecting the desorbed substances to a gel-filtration to collect fractions having a range of molecular weights within the limits of from 10,000 to 300,000.

4. A process according to claim 3 wherein the aqueous solution of the concentrate or dry powder is purified from insoluble matters and inorganic salts contained therein before it is treated.

5. A process for the preparation of an antitumor agent consisting essentially of water-soluble macromolecular glycoprotein substances having a range of molecular weights within the limits of from 10,000 to 300,000 from shellfish which comprises recovering the liquid portion which comes from cooking of raw shellfish in a hot aqueous solvent or with vapor of such solvent and which is to be discarded as waste, concentrating the liquid portion thus recovered to a smaller volume or to dryness to yield a concentrate or dry powder, dissolving the concentrate or dry powder in an aqueous solvent, subjecting the resulting aqueous solution to a gel-filtration to collect fractions having a range of molecular weights within the limits of from 10,000 to 300,000 and subjecting the fractions thus collected to an ion-exchange chromatography with a basic anion-exchanger to adsorb water-soluble macromolecular glycoprotein substances on the exchanger followed by desorption of the substances.

6. A process according to claim 5 wherein the aqueous solution of the concentrate or dry powder is purified from insoluble matters and inorganic salts contained therein before it is treated.

7. A process according to claim 3 or 5 wherein the desorption of the adsorbed substances on the exchanger is effected by elution with a 0.07~0.4 M aqueous sodium chloride solution.

8. A process according to claim 3 or 5 wherein the desorption of the adsorbed substances on the exchanger is effected by elution with a 0.1~0.38 M aqueous sodium chloride solution.

9. A process according to claim 3 or 5 wherein the basic anion-exchanger used in the ion-exchange chromatography is one having diethylaminoethyl or aminoethyl group as ionizing group.

10. An antitumor agent having no cytotoxicity but an immunopotentiating activity and consisting essentially of water-soluble, macromolecular glycoprotein substances which are recovered from the liquid portion which comes from cooking of shellfish with a hot aqueous solvent or with the vapor of such solvent and which have the following characteristics:

(1) Molecular weight: About 10,000 to about 300,000 as measured by gel-filtration chromatography,
(2) Ultraviolet absorption spectrum: With a characteristic absorption peak $\lambda_{max}^{H_2O}$ at 278 nm,
(3) Infrared absorption spectrum (pelleted in KBr): With characteristic absorption peaks at 3500~3300, 1650, 1540 and 1400 cm$^{-1}$,
(4) Solubility: Soluble easily in water but insoluble in organic solvents such as methanol, ethanol and acetone,
(5) Color reactions: Positive in biuret reaction, xanthoproteic reaction, phenolic reagent reaction, anthrone-sulfuric acid reaction and phenol-sulfuric acid reaction; but pseudo-positive in cysteine-sulfuric acid reaction,
(6) Acidic or basic nature: Amphoteric electrolyte,
(7) Substance color and appearance: White-colored solid with or without faint brown tinge,
(8) Amino acids in hydrolysate: When hydrolyzed in 6 N HCl at 105°~110° C. for 24 hours, the resulting hydrolysate contains at least the following amino acids:
aspartic acid, hydroproline, threonine, serine, glutamic acid, proline, glycine, alanine, cysteine, valine, methionine, isoleucine, leucine, tyrosine, phenylalanine, lysine, arginine, histidine, hydroxylysine,
(9) Carbohydrates in hydrolysate: When hydrolyzed in 2 N HCl at 80°~90° C. for 10 hours, followed by the removal of the amino acids from the hydrolysate by ion-exchange chromatography and further by hydrogenation of the amino acids-free hydrolysate, the hydrogenated hydrolysate contains at least the following carbohydrates:
fructose, mannose, fucose, inositol, galactose.

* * * * *